United States Patent [19]

Kidani et al.

[11] 4,169,846
[45] Oct. 2, 1979

[54] CIS-PLATINUM (II) COMPLEX OF TRANS-L-1,2-DIAMINOCYCLOHEXANE

[76] Inventors: Yoshinori Kidani, 2-1, Mataho-machi, Nishi-ku, Nagoya-shi, Aichi-ken; Kenji Inagaki, 5, Shofuen, Hiroji-cho, Showa-ku, Nagoya-shi, Aichi-ken, both of Japan

[21] Appl. No.: 924,320

[22] Filed: Jul. 13, 1978

Related U.S. Application Data

[63] Continuation of Ser. No. 775,216, Mar. 7, 1977, abandoned.

[30] Foreign Application Priority Data

Sep. 6, 1976 [JP] Japan ................................ 51/106509

[51] Int. Cl.$^2$ ............................................ C07F 15/00
[52] U.S. Cl. ................................ 260/429 R; 424/287; 548/301
[58] Field of Search ................................ 260/429 R

[56] References Cited

U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |
| 4,115,418 | 9/1978 | Gale et al. | 260/429 R |
| 4,140,707 | 2/1979 | Cleare et al. | 260/429 R |

OTHER PUBLICATIONS

Cleare et al., Plat. Met. Rev. 17, 2-13, (1973).
Cleare et al., Chem. Abst. 80, 66593d (1974).
Ridgway et al., Chem. Abst. 84, 130450s (1976).
Gale et al., Chem. Abst. 81, 114588a (1974).
Connors et al., Platinum Coordination Complexes in Cancer Chem., Springer-Verlag N.Y., pp. 51 & 135 (1974).
Belluco, Organometallic & Coordination Chemistry of Platinum, Academic Press, N.Y., pp. 93-95, 547-549 (1974).
Leh et al., J. of Pharmaceutical Sciences, 65(3), pp. 315-328 (1976).
Ward et al., Cancer Treatment Reports, 60(11), pp. 1675-1678 (1976).
Speer et al., Chem. Abst. 84, 54030n (1976).
Connors et al., Chem. Abst. 78, 79753q (1973).
Rosenberg, Plat. Metals Rev. 15, 42-47 (1971).

*Primary Examiner*—Helen M. S. Sneed
*Attorney, Agent, or Firm*—Sughrue, Rothwell, Mion, Zinn and Macpeak

[57] ABSTRACT

Cis-platinum (II) complexes of 1,2-diaminocyclohexanes, more particularly, cis-platinum (II) complexes represented by the general formula

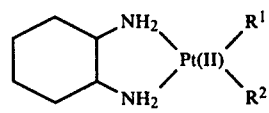

wherein the stereoisomerism of 1,2-diaminocyclohexane is cis-, trans-d- or trans-l-; and $R^1$ and $R^2$, which are same, each represent a halogen atom, or $R^1$ and $R^2$, when taken together, represent a group represented by the formula

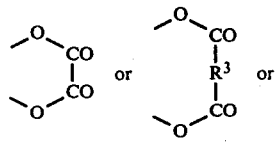

wherein $R^3$ represents a $>CH_2$ group, a $>CHCH_3$ or $>CHCH_2CH_3$ group are disclosed. Further complexes of uracil and cis-[platinum(II)-cis-, trans-d or trans-l-1,2-diaminocyclohexane] are disclosed. These complexes have anti-tumor activity in mice. Cis-platinum (II) complex of cis-1,2-diaminocyclohexane is most effective.

1 Claim, 10 Drawing Figures

CIS-PLATINUM (II) COMPLEX OF TRANS-L-1,2-DIAMINOCYCLOHEXANE

This is a continuation of application Ser. No. 775,216, filed Mar. 7, 1977, now abandoned.

BACKGROUND OF THE INVENTION

1. Field of the Invention

This invention relates to cis-platinum (II) complexes of isomers(cis-, trans-d- and trans-l-isomers) of 1,2-diaminocyclohexane. More particularly, it relates to cis-platinum (II) complexes of isomers (cis-, trans-d-, and trans-l-isomers) of 1,2-diaminocyclohexane represented by the general formula

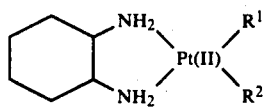

wherein the stereoisomerism of 1,2-diaminocyclohexane is cis-, trans-d-, or trans-l-; and $R^1$ and $R^2$ represent same halogen atoms, or $R^1$ and $R^2$ may, when taken together, form a group represented by the formula

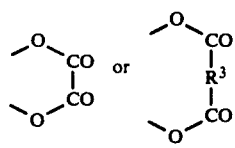

where $R^3$ represents a $>CH_2$ group, a $>CHCH_3$ or $>CHCH_2CH_3$ group. Further it relates to complexes of uracil and cis[platinum(II)-cis, trans-d-, or trans-l-1,2-diaminocyclohexane] (hereinafter referred to as "cis-uracil(cis-, trans-d- or trans-l-1,2-diaminocyclohexane) platinum(II) complex")

2. Description of the Prior Art 1,2-Diaminocyclohexane platinum (II) complexes have hitherto been known as compounds having an anti-tumor activity.

Synthesis method and anti-tumor activity of 1,2-Diaminocyclohexane platinum (II) complexes are disclosed in "Chem.-Biol. Interaction", vol. 5, 415–424 (1972) by Connors, T. A. et.al., "Bioinorg. Chem." Vol. 2, 187–210 (1973) by Clearo, M. J. et.al and "Res. Commun. Chem. Pathol. Pharmacol." Vol. 7, 529–538 (1974) by Gale, G. R. et.al.

Since the starting material of the above platinum (II) complex, 1,2-diaminocyclohexane (hereinafter referred to as "1,2-DAC" for brevity) has been available as a mixture of cis-, trans-d- and trans-l-isomers thereof, the corresponding platinum (II) complex derived from the starting material is a mixture of three isomers, i.e., a cis-isomer, a trans-d-isomer and a trans-l-isomer. The cis-isomer is a geometrical isomer and the trans-d- and trans-l-isomers are optical isomers.

It has been reported that 1,2-diaminocyclohexane platinum (II) complex has an anti-tumor activity. This activity of 1,2-diaminocyclohexane platinum (II) complex, however, has been confirmed using a mixture of two or more isomers thereof, and it has not been known which cis-platinum (II) complex of 1,2-DAC isomers exhibits sufficient anti-tumor activity and low toxicity.

SUMMARY OF THE INVENTION

A main object of this invention is to provide an isomer of 1,2-diaminocyclohexane platinum (II) complex having superior anti-tumor activity in mice.

Another object of this invention is to provide an isomer of 1,2-diaminocyclohexane platinum (II) complex having low toxicity.

Yet another object of this invention is to provide a suitable preparations of an isomer of 1,2-diaminocyclohexane platinum (II) complex.

As a result of extensive research it was found that cis-platinum (II) complex containing mixed ligands consisting of cis-, trans-d- or trans-l-isomer of 1,2-diaminocyclohexane and a halogen atom, an organic dibasic acid or pyrimidine can be synthesized using cis-, trans-d- or trans-l-isomer of 1,2-diaminocyclohexane which is obtained by the method described in Japanese Patent Application No. 27818/1976 as a starting material.

Further research on anti-tumor effect has led to the finding that 1,2-DAC isomers having different stereo-isomerism have different anti-tumor activity in mice and that the strength of anti-tumor activity in mice of these isomers is increased in the order of trans-l-isomer<trans-d-isomer<cis-isomer.

It was also found that Cis-platinum (II) of cis-, trans-d- and trans-l-1,2-DAC complexes have an anti-microbial activity.

DETAILED DESCRIPTION OF THE INVENTION

Figure 1:
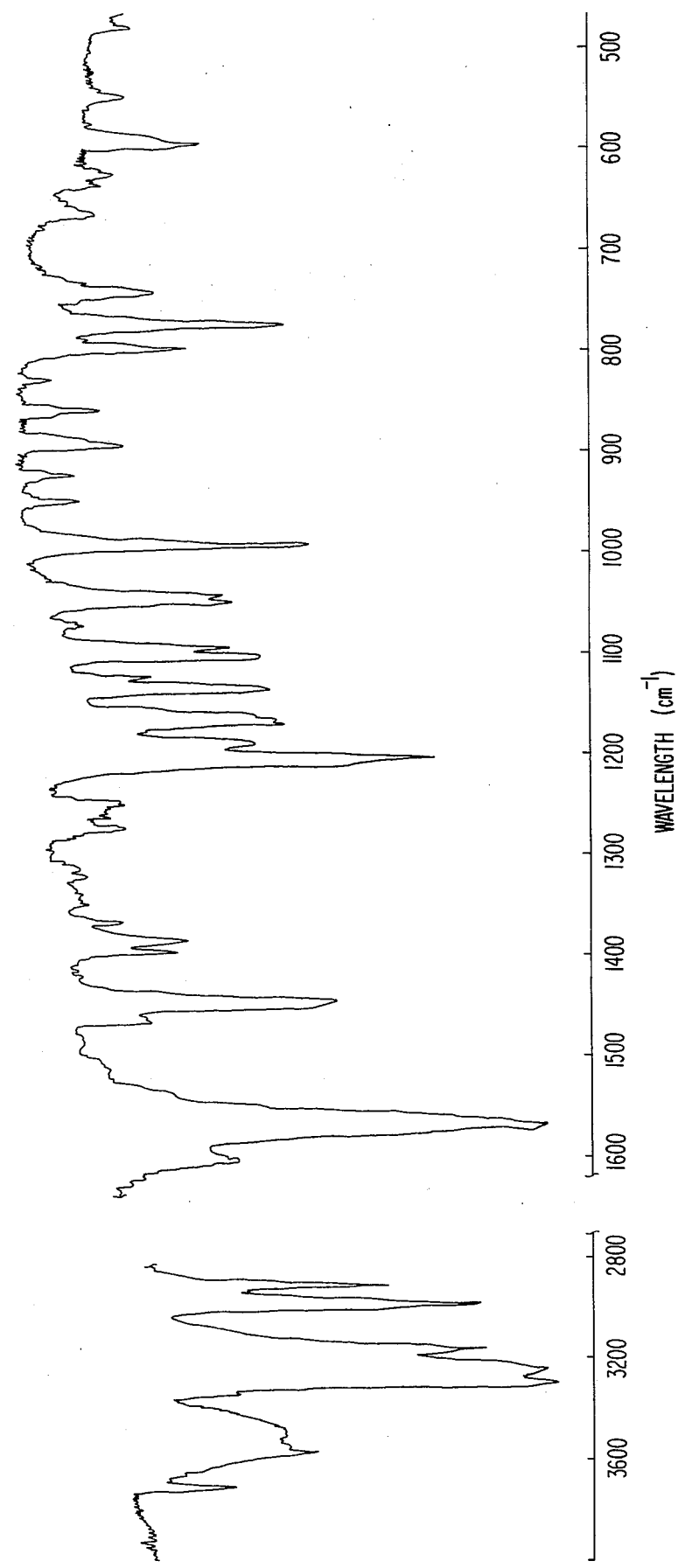
FIG. 1 is a graphical representation of infrared absorption spectrum (KBr) of cis-dichloro(cis-1,2-DAC) platinum (II)
Figure 2:
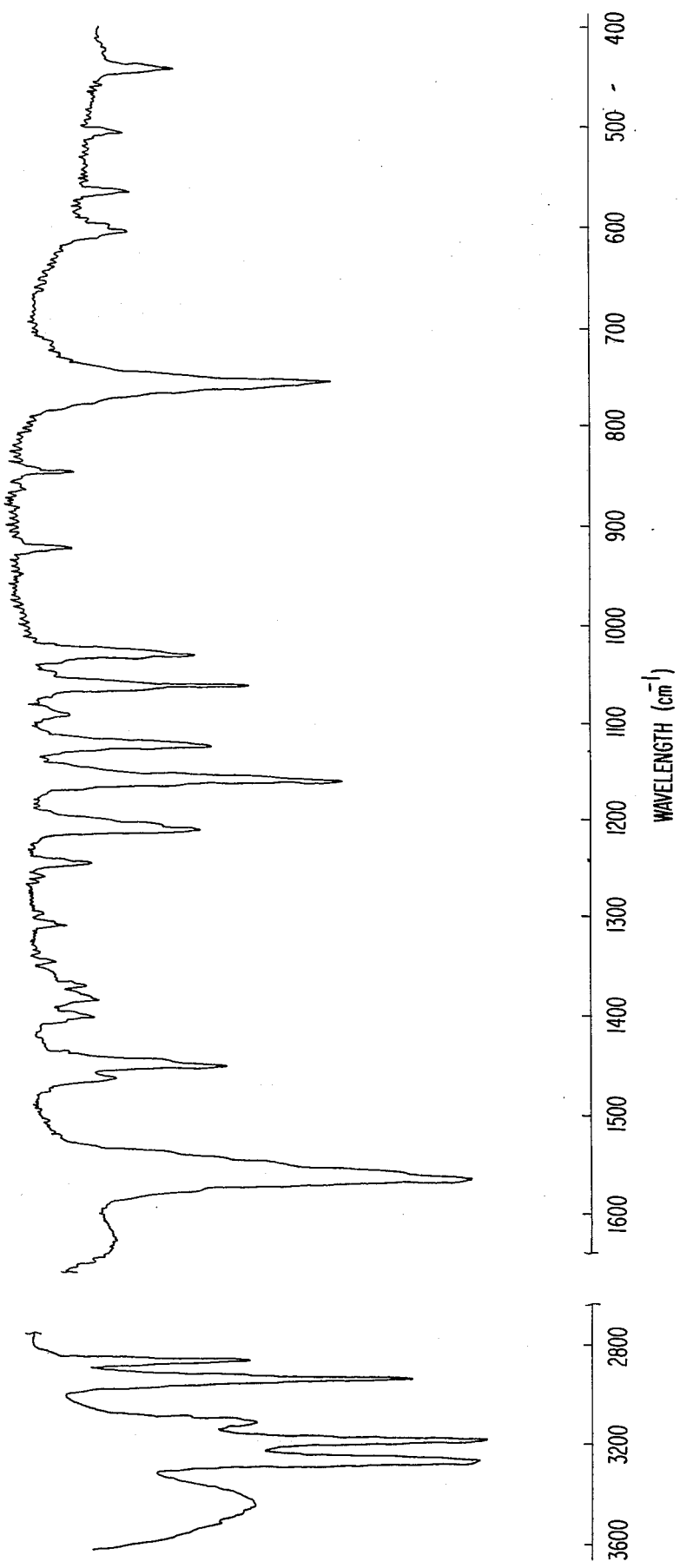
FIG. 2 is a graphical representation of infrared absorption spectrum (KBr) of cis-dichloro-(trans-l-1,2-DAC) platinum (II)
Figure 3:
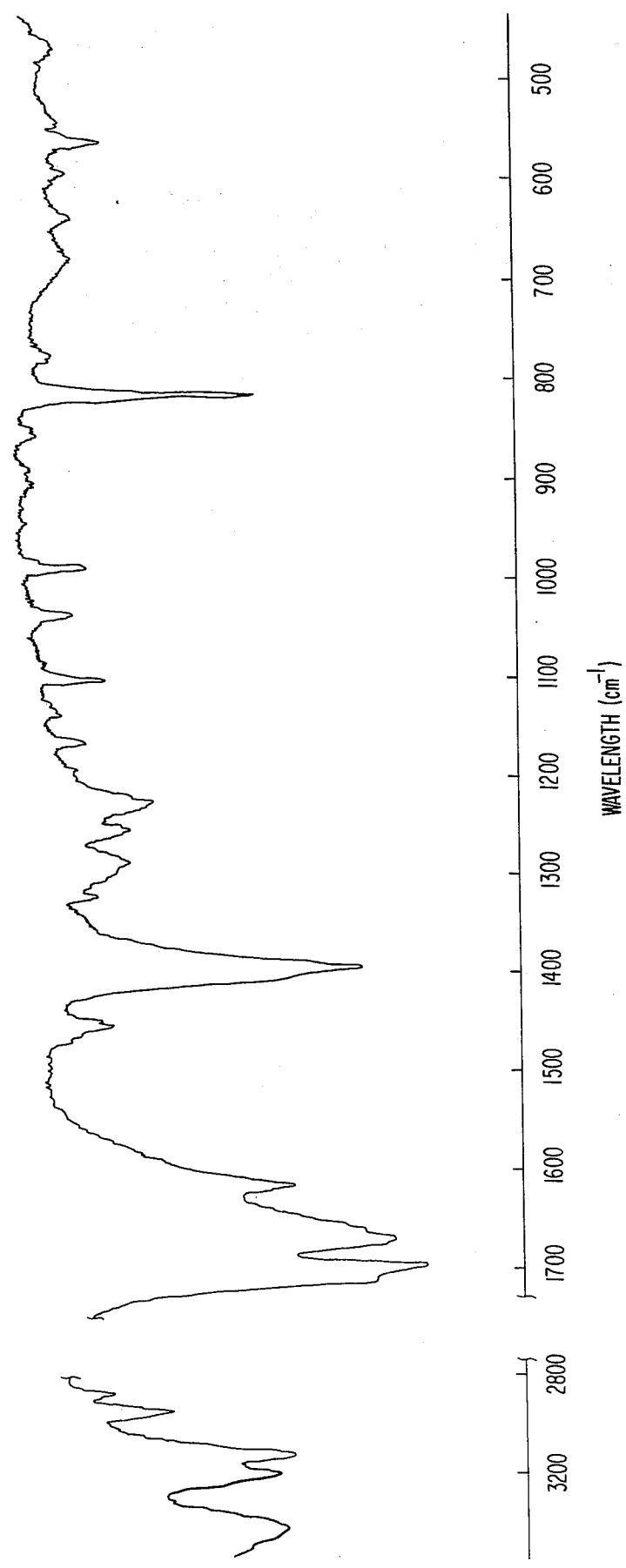
FIG. 3 is a graphical representation of infrared absorption spectrum (KBr) of cis-oxalato-(cis-1,2-DAC) platinum (II)
Figure 4:
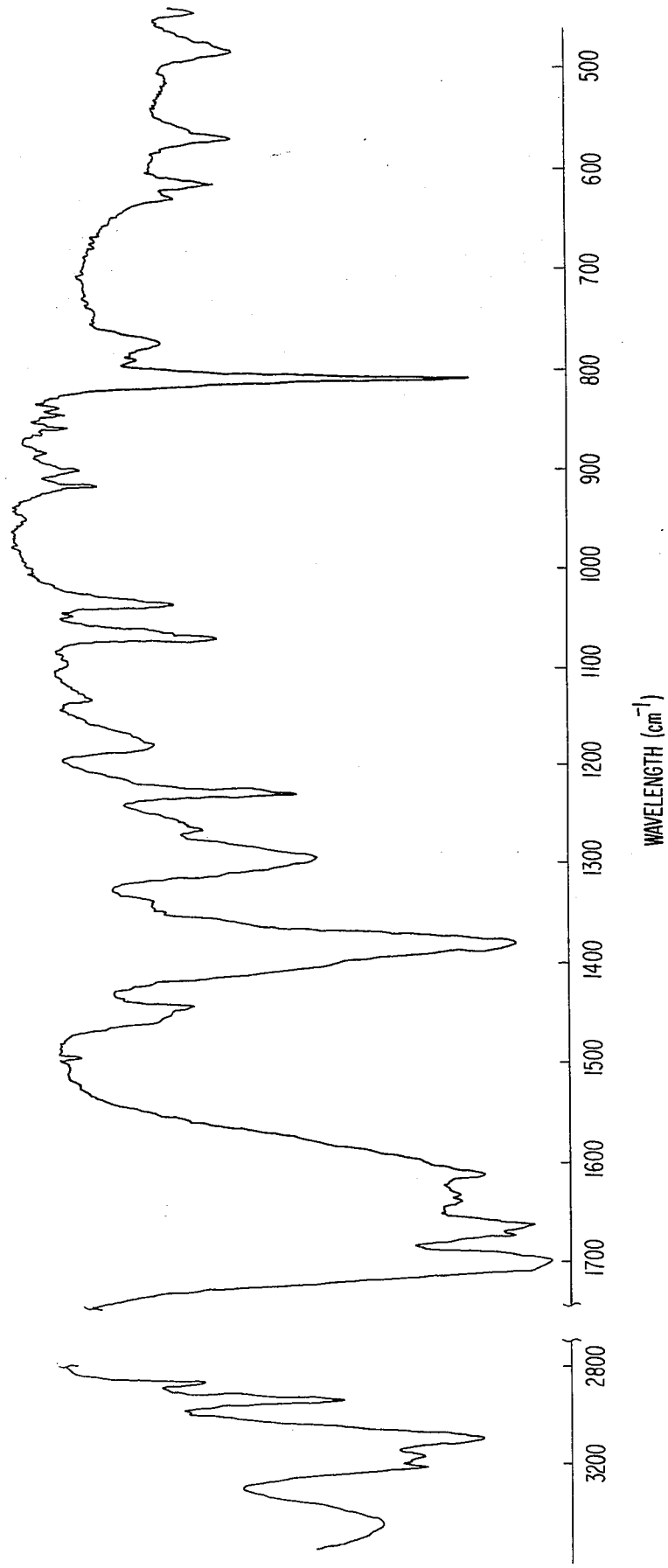
FIG. 4 is a graphical representation of infrared absorption spectrum (KBr) of cis-oxalato-(trans-l-1,2-DAC) platinum (II)
Figure 5:
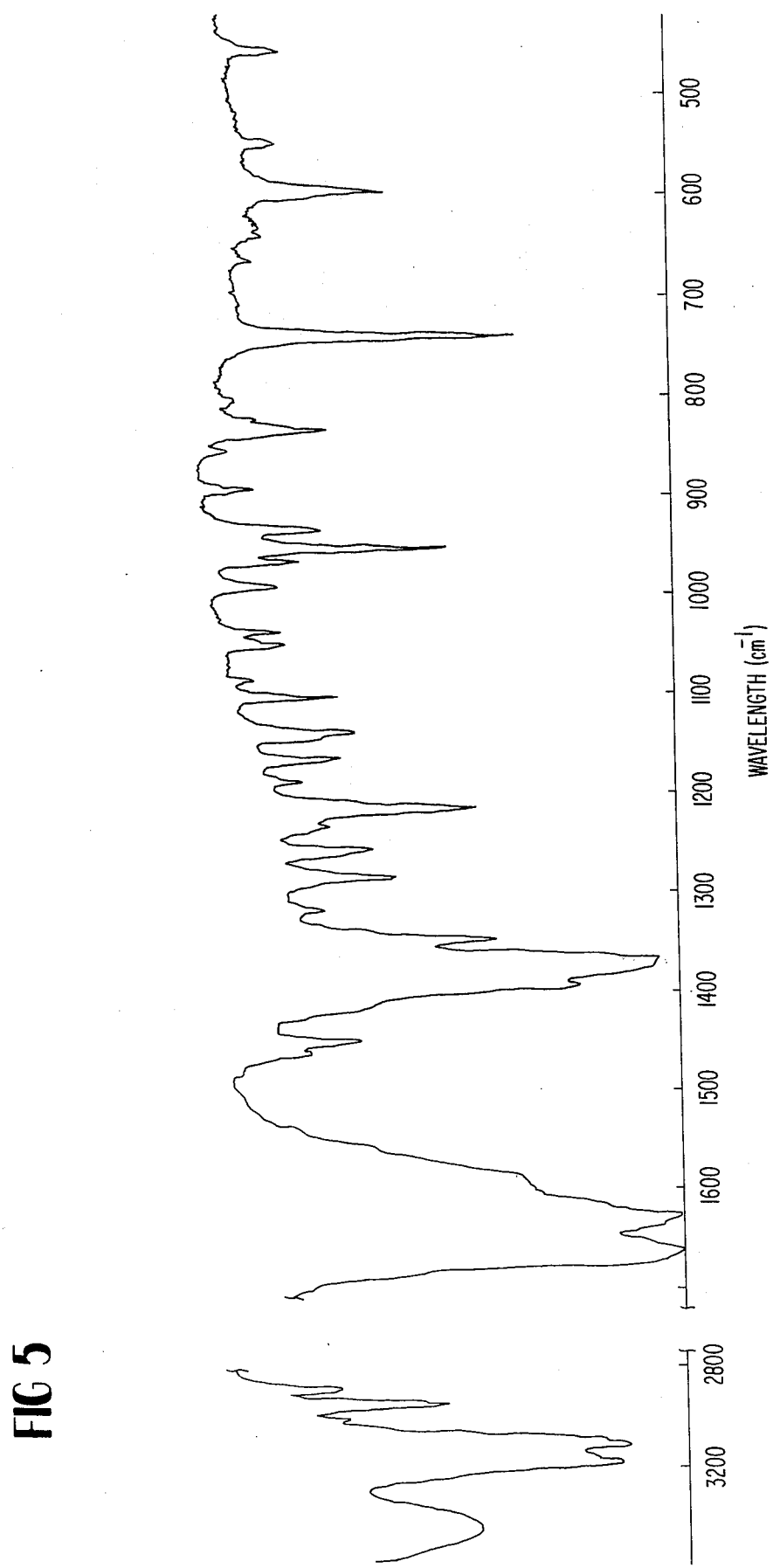
FIG. 5 is a graphical representation of infrared absorption spectrum (KBr) if cis-malonato-(cis-1,2-DAC) platinum (II)
Figure 6:
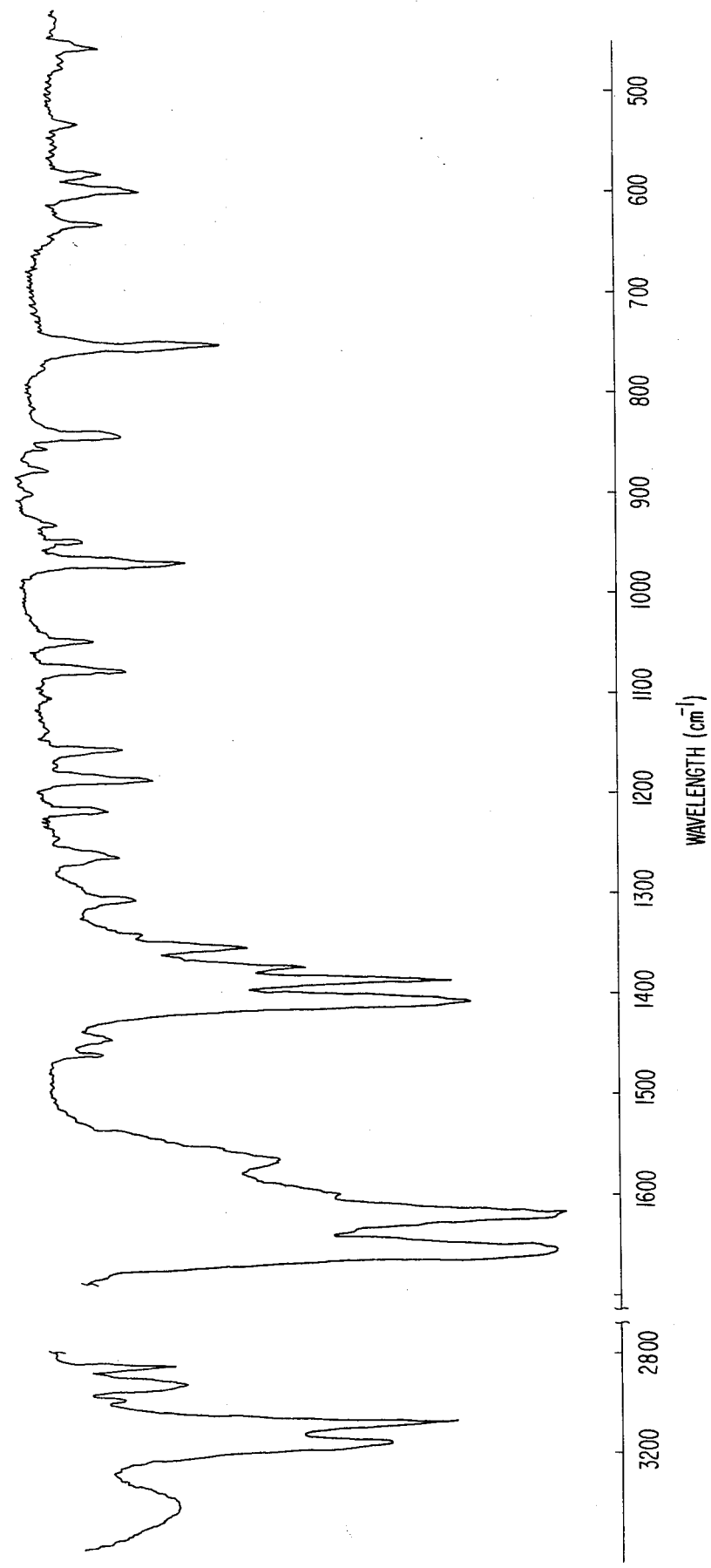
FIG. 6 is a graphical representation of infrared absorption spectrum (KBr) of cis-malonato-(trans-l-1,2-DAC) platinum (II)
Figure 7:
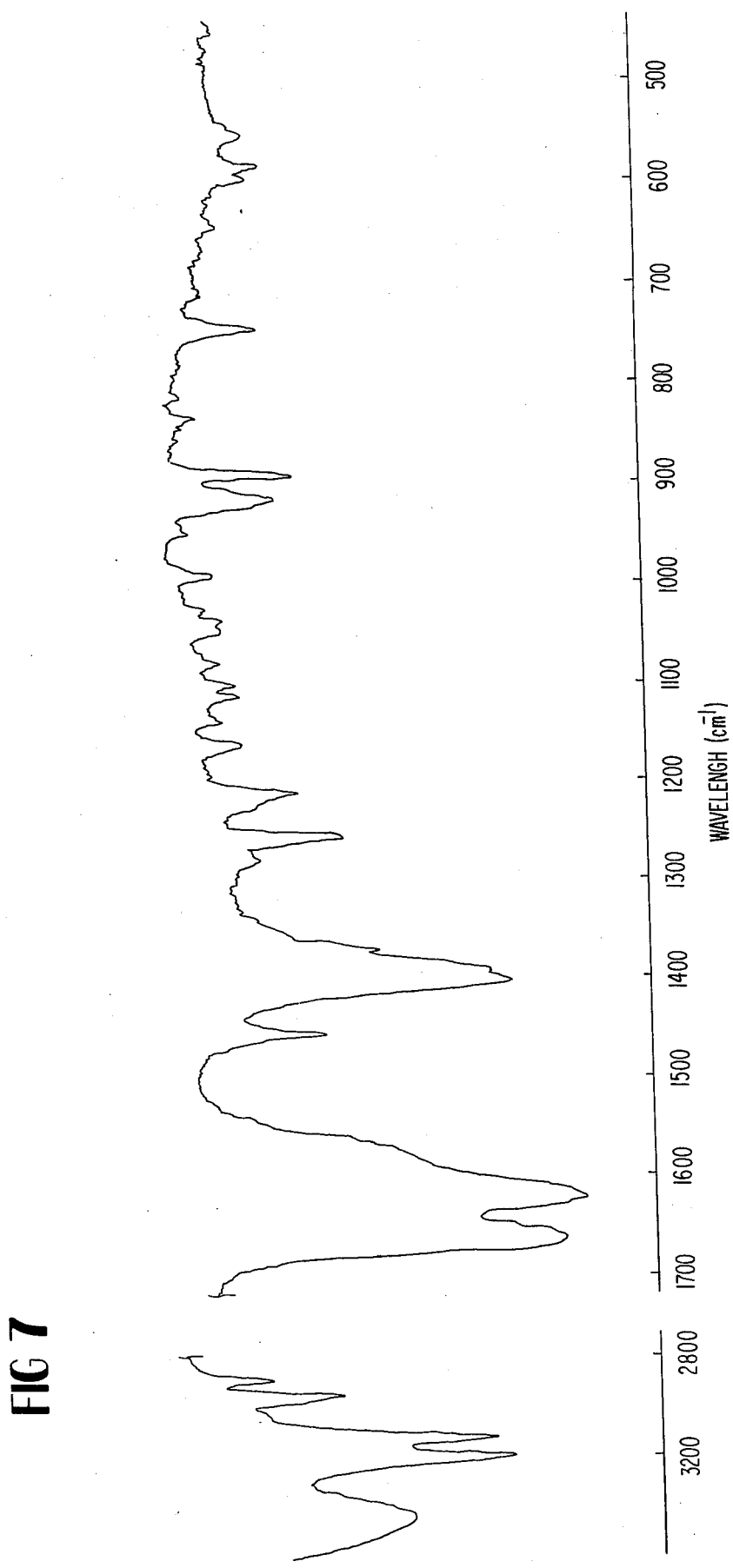
FIG. 7 is a graphical representation of infrared absorption spectrum (KBr) of cis-methylmalonato-(cis-1,2-DAC) platinum (II)
Figure 8:
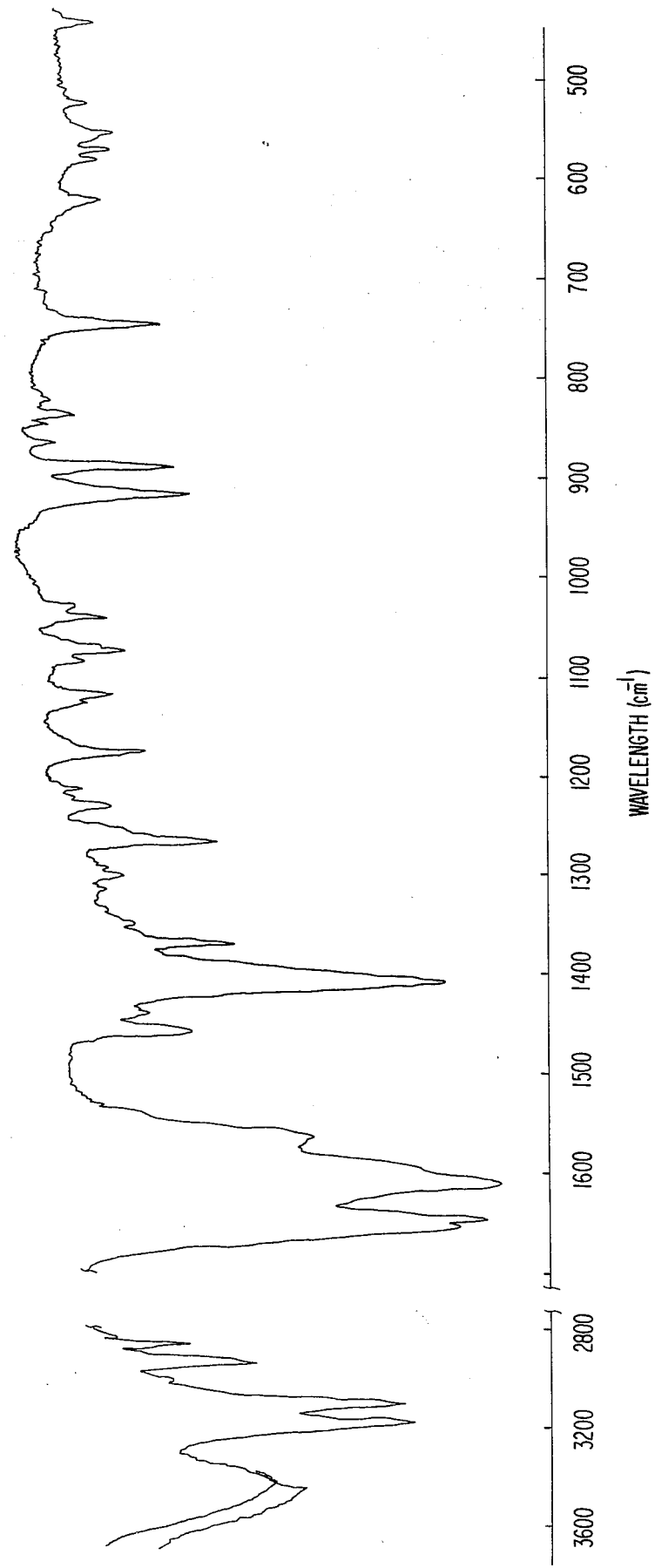
FIG. 8 is a graphical representation of infrared absorption spectrum (KBr) of cis-methylmalonato-(trans-l-1,2-DAC) platinum (II)
Figure 9:
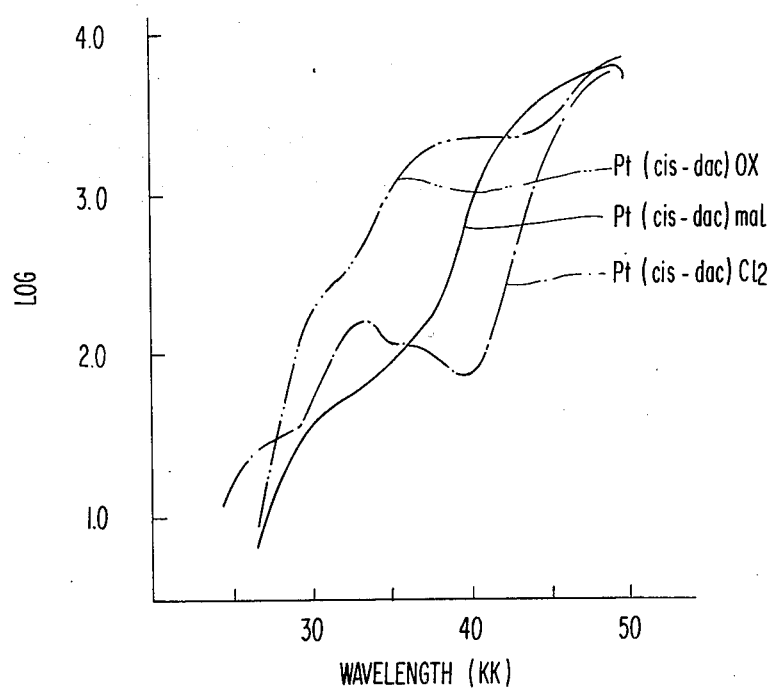
FIG. 9 is a graphical representation of electronic spectra of an aqueous solution of cis-dichloro(cis-1,2-DAC) platinum (II) [Pt(cis-DAC)Cl₂], cis-oxalato(cis-1,2-DAC) platinum (II) [Pt(cis-DAC)OX], and cis-malonato(cis-1,2-DAC) platinum (II) [Pt(cis-DAC)-Mal]
Figure 10:
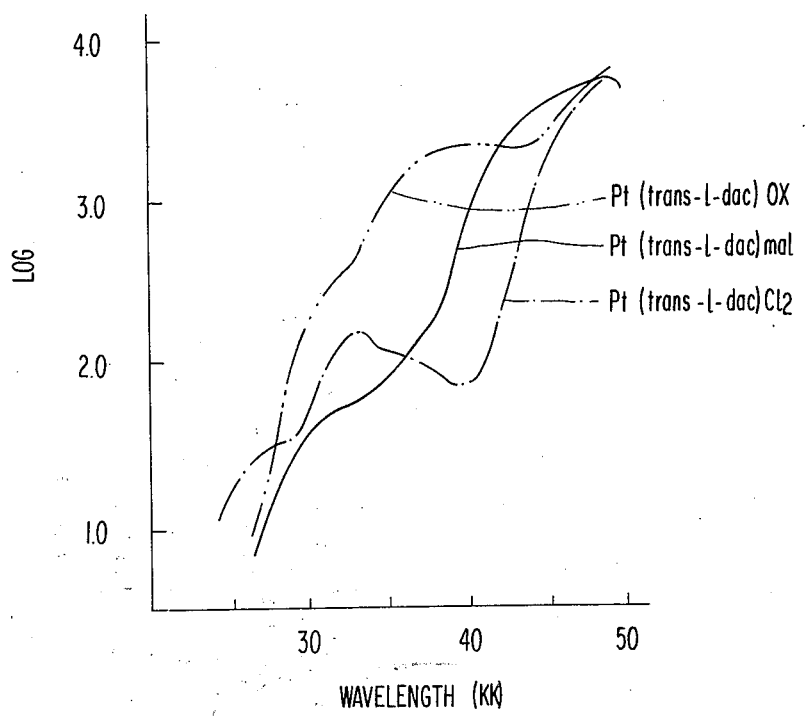
FIG. 10 is a graphical representation of electronic spectra of cis-dichloro(trans-l-1,2-DAC) platinum (II) [Pt(trans-l-DAC)Cl₂], cis-oxalato(trans-l-1,2-DAC) platinum (II) [Pt(trans-l-DAC)OX], cis-malonato(trans-l-1,2-DAC) platinum (II) [Pt(trans-l-DAC)Ma].

Cis-platinum (II) complex of 1,2-DAC isomers according to this invention, that is, cis-platinum (II) complex of 1,2-DAC isomers (cis- trans-d- or trans- -) represented by the general formula

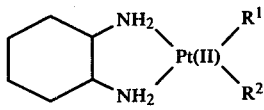

wherein the stereoisomerism of 1,2-DAC is same as above and $R^1$ and $R^2$ are as defined above and cis-uracil (cis-, trans-d- or trans-l-1,2-DAC) platinum (II) can be obtained according to the method set forth below.

As a starting material, cis-, trans-d- and trans-l-isomers of 1,2-DAC can be used. These three isomers can be prepared by isolating and purifying utilizing differences in the physical chemical properties of Ni(II) complexes of 1,2-DAC isomers as described in Japanese Patent Application No. 27818/1976.

That is, 0.22 mol of commercially available 1,2-DAC and 0.11 mol of $NiCl_2.6H_2O$ are added to anhydrous methanol with stirring at room temperature for 2 hours to form precipitate of cis-1,2-DAC which is filtered out. To the filtrate is added 440 ml of 6 N HCl and is adjusted to pH 4.2 to 4.5 with 15% NaOH. The precipitate thus obtained contains trans-d, l-,2-DAC. Trans-d, l-1,2-DAC is divided into trans-d-1,2-DAC and trans-l-1,2-DAC in the conventional manner using d-tartaric acid.

The thus obtained cis-, trans-d- and trans-l-forms are used as starting materials of further procedures. According to the present invention, cis-dihalogeno(cis-trans-d- or trans-l-1,2-DAC) platinum (II) is prepared by reacting 1,2-DAC isomers with metal salt of tetrahalogenoplatinum such as $K_2PtCl_4$, etc. Cis-dicarboxylate (cis-, trans-d- or trans-l-1,2-DAC) platinum (II) is prepared by reacting cis-diaquo (1,2-DAC isomers) platinum (II) with metal salt of dicarboxylic acid.

Cis-uracil(1,2-DAC isomers) platinum (II) complex are prepared by reacting cis-diaquo (1,2-DAC isomers) platinum (II) with uracil. Cis-diaquo (1,2-DAC isomers) platinum (II) is prepared by reacting cis-halogeno(1,2-DAC isomers) platinum (II) with Metal salts of mineral acid such as $AgNO_3$, $Ag_2SO_4$, $Ag_3PO_4$, etc.

More details are now explained in below. Equimolar amounts of the 1,2-DAC (cis-, trans-d- and trans-l-) and $K_2Pt(II)X_4$ wherein X represents a halogen atom such as Cl, Br are dissolved in water and reacts at 5° to 35° C., preferably at room temperature (e.g., 20° to 25° C.) for about 3 to about 48 hours, preferably 12 hours to provide raw crystals of cis-platinum (II) complexes of 1,2-DAC (cis-, trans-d- and trans-l-) represented by the general formula (I)

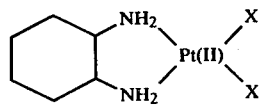

wherein the stereoisomerism of 1,2-DAC is cis-, trans-d- or trans-l- and X is same as above. The raw crystals can be recrystallized from hot aqueous solution of hydrochloric acid (e.g., 0.1 N HCl solution). Upon recrystallization there is a marked difference in the volume of 0.1 N HCl used between cis- and trans forms. For example, about 300 ml of 0.1 N HCl is necessary for recrystallizing 1 g of cis-platinum (II) complex of cis-1,2-DAC while 2,000 ml of 0.1 N HCl is required to recrystallize 1 g of cis-platinum (II) complex of trans-1,2-DAC.

The compound having the formula (I) is added in water followed by boiling to dissolve same. To the resulting solution is added 2 mol equivalent of aqueous solution of silver nitrate with stirring for 2 to 3 hours in the dark. After cooling the filtration of reaction mixture is repeated till the filtrate becomes transparent followed by concentrating under reduced pressure. The concentrate contains cis-diaquo(1,2-DAC isomers) platinum (II). To the concentrate is added metal salt of dicarboxylic acid such as potassium oxalate, potassium malonate, potassium methylmalonate, potassium ethylmalonate, etc. in an equimolar amount based on the compound represented by the general formula (I) and the resulting mixture is overnighted at room temperature followed by concentrating under reduced pressure to form crystalline precipitate of cis-platinum (II) complex of 1,2-DAC represented by the general formula (II)

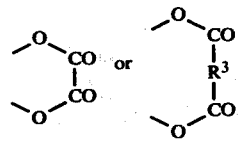

wherein the stereoisomerism of 1,2-DAC is cis-, trans-d-, trans-l-, and $R^1$ and $R^2$, taken together, represent a group

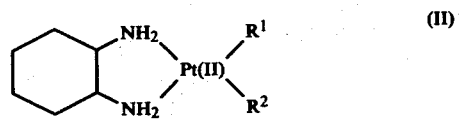

where $R^3$ represents a $>CH_2$, $>CHCH_3$ or $>CHCH_2CH_3$ group.

Further, 0.01 mol of the compound represented by the general formula (1) and 0.02 mol of silver nitrate are dissolved in water and the resulting solution is stirred for 3 hours at room temperature in the dark followed by allowing to stand for 1 hour at 0° C. and filtering. The filtrate contains cis-diaquo(1,2-DAC isomers) platinum (II). To the filtrate is added aqueous solution of 0.01 mol of uracil dissolved in 2 N NaOH, and pH of the resulting mixture is adjusted to pH 7 to 8. The reaction mixture is allowed to stand for at least 1 week at about 37° C. follows by allowing to stand at 0° C. for about 8 hours to form complex of uracil and a group represented by the following formula

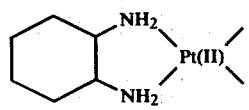

wherein the stereoisomerism of 1,2-DAC is same as above.

Generally, the complex of pyrimidine and platinum (II) is known as platinum blue. The chemical structure of this complex including the complex of uracil and Pt(II) in this invention has not, however, been clarified yet.

Examples of the cis-platinum (II) complex of cis-trans-d-or trans-l-1,2-DAC include the following compounds.

Compound No. 1: Cis-dichloro(cis-1,2-diaminocyclohexane)Platinum (II)
Compound No. 2: Cis-dichloro(trans-d-1,2-diaminocyclohexane)platinum (II)
Compound No. 3: Cis-dichloro(trans-l-1,2-diaminocyclohexane)platinum (II)
Compound No. 4: Cis-oxalato(cis-1,2-diaminocyclohexane)platinum (II)
Compound No. 5: Cis-oxalato(trans-d-1,2-diaminocyclohexane)platinum (II)
Compound No. 6: Cis-oxalato(trans-l-1,2-diaminocyclohexane)platinum (II)
Compound No. 7: Cis-malonato(cis-1,2-diaminocyclohexane)platinum (II)
Compound No. 8: Cis-malonato(trans-d-1,2-diaminocyclohexane)platinum (II)
Compound No. 9: Cis-malonato(trans-l-1,2-diaminocyclohexane)platinum (II)
Compound No. 10: Cis-methylmalonato(cis-1,2-diaminocyclohexane)platinum (II)
Compound No. 11: Cis-methylmalonato(trans-d-1,2-diaminocyclohexane)platinum (II)
Compound No. 12: Cis-methylmalonato(trans-l-1,2-diaminocyclohexane)platinum (II)
Compound No. 13: Cis-uracil(cis-1,2-diaminocyclohexane)platinum (II)
Compound No. 14: Cis-uracil(trans-d-1,2-diaminocyclohexane)platinum (II)
Compound No. 15: Cis-uracil(trans-l-1,2-diaminocyclohexane)platinum (II)

Cis-platinum (II) complexes of 1,2-DAC isomers according to this invention exhibit anti-tumor activity against experimental tumors on mouse, such as L1210, P388 and S180A (ascites-tumor), and therefore are useful in chemotherapeutics of tumors.

Also, cis-platinum (II) complexes of 1,2-DAC isomers according to this invention exhibit an antimicrobial activity and are useful as a cleaning agent.

The platinum (II) complexes of this invention can be administered orally, intramuscularly or intravenously. They can be formulated as capsules, powders, pellets or injections.

Suitable dosage of the platinum (II) complexes of this invention is about 1 to 400 mg/kg/day.

EXPERIMENT 1

(Acute Toxicity Test)

The $LD_{50}$ on male mice (ddN strain) is given in Table 3 below. A suspension of the test substance in 0.3% CMC aqueous solution was intraperitoneally administered to the test mice in a dose amount of 0.5 ml per mouse.

TABLE 1

| Compound No. | $LD_{50}$ (mg/kg) |
|---|---|
| 1 | 11.3 |
| 2 | 22.5 |
| 3 | 14.1 |
| 4 | 37.5 |
| 5 | 22.5 |
| 6 | 26.3 |

EXPERIMENT 2

(Anti-tumor Activity on Mice against leukemia L 1210 and P 388)

To test the anti-tumor activity of the compounds of the present invention, 100,000 cells/mouse of leukemia L 1210 and 1,000,000 cells/mouse of leukemia P 388 were transplanted by intraperitoneal injection to groups of $CDF_1$ mice, respectively. One and 5 days after the transplantation, the test compound was administered by intraperitoneal injection to the mice.

The anti-tumor activity of the test compound was evaluated by means of T/C %, i.e., 100 times the mean survival period of the groups injected with the test compound divided by the means survival period of the comparison groups which were not injected with the test compound. The value of higher than 120% for L 1210 and higher than 125% for P 388 means that the test compound has a good effect. The results thus obtained are shown in Table 2 below.

TABLE 2

| Compound No. | 400 | 200 | 150 | 100 | 80 | 75 | 50 | 40 | 37.5 | 25 | 20 | 12.5 | 10 | 6.25 | Remarks |
|---|---|---|---|---|---|---|---|---|---|---|---|---|---|---|---|
| 1 | 0 | 0 | | 0 | | | | | | $164^P$ | | $211^P$ | | $198^P$ | * |
| 2 | | 0 | | 71 | | | 71 | | | | 110 | $291^P$ | | | * |
| 3 | | 0 | | 0 | | | 71 | | | | 88 | $379^P$ | | $316^P$ | * |
| 4 | | | | 0 | | | 0 | | | $200^P$ | | | | | ** |
| 5 | | | | | | | | | 0 | | $195^P$ | | $174^P$ | | ** |
| 6 | | | | 0 | | | 0 | | | 61 | | | | $188^P$ | ** |
| 7 | | | | | | | $155^P$ | | | $142^P$ | | $126^P$ | | | ** |
| 8 | | | | | | | $155^P$ | | | $138^P$ | | 121 | | | ** |
| 9 | | | 104 | | | | $202^P$ | | $144^P$ | | | | | | ** |
| 10 | | | | | $133^P$ | | | 121 | | | 102 | | | | ** |
| 11 | | | $154^P$ | | | | $138^P$ | | | 121 | | | | | ** |
| 12 | | | $141^P$ | | | | 122 | | | 115 | | | | | ** |
| 13 | 0 | 71 | $163^P$ | | | | | | | | | | | | ** |
| 14 | | $178^P$ | $142^P$ | | | | $140^P$ | | | | | | | | ** |
| 15 | | $178^P$ | $181^P$ | | | | $155^P$ | | | | | | | | ** |

*L 1210
**P 388
$^P$ Effective

EXPERIMENT 3

(Anti-tumore Activity on Mice against Ascites-tumor S 180A)

To test the anti-tumor activity of the compounds of the present invention, cells of ascites-tumor Sarcoma 180A were transplanted by intraperitoneal injection to groups of ddN mice. From one to five days, the test compound was administered by intraperitoneal injection day after day. The ascites of the resulting mice was sampled to evaluate the anti-tumor activity of the test compound by means of the growth rate of the tumor, T/C % (groups with treatment/groups without treatment). The results thus obtained are shown in Table 3 below. In the table, the designations "−", "+", "++" and "+++" mean 100-66%, 65-41%, 40-11% and 10-0%, of the T/C %, respectively.

TABLE 3

| Compound No. | Dose Amount mg/kg i.p. | Growth Rate T/C (%) | Evaluation |
|---|---|---|---|
| 1 | 30 | — | Toxic (6/6 deceased) |
|  | 10 | 0 | +++ |
|  | 3 | 3 | +++ |
|  | 1 | 57 | + |
| 2 | 10 | — | Toxic (5/6 deceased) |
|  | 3 | 1 | +++ |
|  | 1 | 8 | ++ |
| 3 | 10 | — | Toxic (6/6 deceased) |
|  | 3 | 2 | +++ |
|  | 1 | 18 | ++ |
| 4 | 30 | — | Toxic (6/6 deceased) |
|  | 10 | 0 | +++ |
|  | 3 | 0 | +++ |
|  | 1 | 0 | +++ |
|  | 0.3 | 83 | — |
| 5 | 10 | — | Toxic (5/6 deceased) |
|  | 3 | 10 | +++ |
| 6 | 10 | — | Toxic (4/6 deceased) |
|  | 3 | 9 | +++ |
| 7 | 100 | 0 | +++ |
|  | 30 | 0 | +++ |
|  | 10 | 61 | + |
| 8 | 100 | 0 | +++ |
|  | 30 | 1 | +++ |
|  | 10 | 47 | + |
| 9 | 100 | 4 | +++ |
|  | 30 | 1 | +++ |
|  | 10 | 17 | ++ |
|  | 3 | 85 | — |
| cis-dichloro (1,2-DAC) Pt(II) (Control) | 10 | — | Toxic (6/6 deceased) |
|  | 3 | 3 | +++ |
|  | 1 | 19 | ++ |
|  | 0.3 | 12 | ++ |

EXAMPLE 1

Preparation of Cis-dichloro (cis-1,2-diaminocyclohexane)platinum (II)

An aqueous solution of 5 g of cis-1,2-diaminocyclohexane and 18 g of $K_2(PtCl_4)$ was allowed to react at room temperature for about 12 hours to precipitate yellow needle-like crystals. The thus obtained precipitate was filtered and recrystallized from 3.6 l of boiled 0.1 N HCl to obtain 12 g of the titled compound having a melting point of higher than 300° C.

EXAMPLE 2

Preparation of Cis-dichloro(trans-d-1,2-diaminocyclohexane)platinum-(II) and Cis-dichloro(trans-l-1,2-diaminocyclohexane)platinum (II)

The same reaction procedure as in Example 1 was followed except but using, as a starting material, trans-d-1,2-diaminocyclohexane or trans-l-1,2-diaminocyclohexane in place of cis-1,2-diaminocyclohexane to synthesize a platinum (II) complex corresponding to the starting material. The thus synthesized complex was recrystallized from 25 l of boiled 0.1 N HCl to obtain 13 g of each of the titled compounds, each compound having a melting point of higher than 300° C.

EXAMPLE 3

Preparation of Cis-oxalato(cis-1,2-diaminocyclohexane)platinum (II)

To 3 g of cis-dichloro(cis-1,2-diaminocyclohexane)platinum (II) was added 500 ml of water, and the mixture was then boiled to thereby complete the dissolution. To the resulting solution was added 2.6 g of $AgNo_3$ (corresponding to the amount of twice molar times), and the resulting mixture was stirred for 3 hours in the dark. After cooling the mixture, the filtration was repeated using a filter paper (No. 5C, produced by Toyo Roshi Kaisha Ltd.) until the filtrate became transparent. The filtrate thus obtained was concentrated under reduced pressure to an extent of a 100 ml amount, and 1.3 g of potassium oxalate was then added thereto followed by allowing the mixture to stand at room temperature for 8 hours. Thereafter, the resulting solution was further concentrated under reduced pressure to form a white crystalline precipitate. The thus formed precipitate was recrystallized from an aqueous solution to obtain 1.5 g of white scale-like crystals having a melting point of higher than 300° C.

EXAMPLE 4

The same reaction and recrystallization as in Example 3 were followed to obtain the following complexes (i) to (viii), each having a melting point of higher than 300° C.

(i) Cis-oxalato(trans-l-1,2-diaminocyclohexane)platinum (II)
(ii) Cis-oxalato(trans-d-1,2-diaminocyclohexane)platinum (II)
(iii) Cis-malonato(cis-1,2-diaminocyclohexane)platinum (II)
(iv) Cis-malonato(trans-l-1,2-diaminocyclohexane)platinum (II)
(v) Cis-malonato(trans-d-1,2-diaminocyclohexane)platinum (II)
(vi) Cis-methylmalonato(cis-1,2-diaminocyclohexane)platinum (II)
(vii) Cis-methylmalonato(trans-l-1,2-diaminocyclohexane)platinum (II)
(viii) Cis-methylmalonato(trans-d-1,2-diaminocyclohexane)platinum (II)

EXAMPLE 5

Preparation of a Complex of Uracil and Cis-[platinum (II)-cis-1,2-diaminocyclohexane]

100 ml of an aqueous solution of 3 g of cis-dichloro(cis-1,2-diaminocyclohexane)platinum (II) and 2.6 g of $AgNO_3$ was stirred at room temperature for 3 hours in a dark room followed by keeping the resulting solution at 0° C. for 1 hour. Silver chloride was filtered out from the solution, and then, the presence of excess silver in the solution was examined by sampling a small amount of the residual solution to which 0.1 N HCl was added. The thus obtained nitric acid salt of cis-(diaquo-1,2-diaminocyclohexane)platinum (II) was neutralized with 2.0 N NaOH.

The resulting solution was mixed with a solution prepared by dissolving 1.77 g of uracil in 100 ml of water and adjusting to the pH of 9.0 with 2.0 N NaOH, and the mixture was then adjusted to the pH of 7 to 8. A vessel containing the solution was shielded and shaded by an aluminum foil followed by allowing the solution to react at 37° C. for more than one week in such a vessel. Subsequently, the resulting reaction solution was cooled to 0° C. over about 8 hours, and ethanol was then added thereto to obtain 0.7 g of a slightly yellow precipitate having a melting point of higher than 300° C.

EXAMPLE 6

Preparation of (1) a Complex of Uracil and Cis-[platinum (II)-trans-l-1,2-diaminocyclohexane] and (2) a complex of Uracil and Cis-[platinum (II)-trans-d-1,2-diaminocyclohexane]

Complexes (1) and (2) were obtained in the same manner as in Example 5. Each complex was found to have a melting point of higher than 300° C.

The structural formula and elementary analysis value of each compound obtained in Examples 1 to 6 are summarized in Table 4 below. Since the structural formula of the compounds obtained in Examples 5 and 6 is unknown, their elementary analysis value is not described in the table.

Turning now, the infrared absorption spectrum of the platinum (II) complexes obtained in the above-described Examples is explained hereinbelow.

Cis-dichloro(cis-1,2-diaminocyclohexane)platinum (II) exhibit absorption bands at 3245, 3193 and 3118 cm$^{-1}$ ($\nu NH_2$); 1569 cm$^{-1}$ ($\partial NH_2$); and 760 cm$^{-1}$ ($\rho NH_2$). Cis-dichloro(trans-l-1,2-diaminocyclohexane)platinum (II) and cis-dichloro(trans-d-1,2-diaminocyclohexane)platinum (II) exhibit absorption bands at 3267, 3185 and 3104 cm$^{-1}$ ($\nu NH_2$); 1564 cm$^{-1}$ ($\partial NH_2$); 756 cm$^{-1}$ ($\rho NH_2$), respectively. The distinction of cis-dichloro(cis-1,2-diaminocyclohexane)platinum (II) from cis-dichloro(trans-l-1,2-diaminocyclohexane)platinum (II) and cis-dichloro(trans-d-1,2-diaminocyclohexane)platinum (II) is apparent from the absorption bands of $\nu_{c-c}$ and/or $\rho CH_2$ in a region of from 800 to 1000 cm$^{-1}$. That is, cis-dichloro(trans-l-1,2-diaminocyclohexane)platinum (II) and cis-dichloro(trans-d-1,2-diaminocyclohexane)platinum (II) exhibit only two absorption bands at 926 and 849 cm$^{-1}$ in a region of from 800 to 1000 cm$^{-1}$. In contrast, cis-dichloro(cis-1,2-diaminocyclohexane)platinum (II) characteristically exhibit six absorption bands at 984, 940, 914, 885, 849 and 818 cm$^{-1}$ in this region. This is theoretically in accord with that cis-dichloro(trans-l-1,2-diaminocyclohexane)platinum (II) and dichloro(trans-d-1,2-diaminocyclohexane)platinum (II) are higher than cis-dichloro(cis-1,2-diaminocyclohexane)platinum (II) in the symmetry of complex.

Any of cis-oxalato(cis-1,2-diaminocyclohexane)platinum (II), cis-malonato(cis-1,2-diaminocyclohexane)platinum (II) and cis-methylmalonato(cis-1,2-diaminocyclohexane)platinum (II) exhibits the absorption bands based on the amino group and the carbonyl group. The platinum (II) complexes corresponding to trans-l-1,2- and trans-d-1,2-diaminocyclohexanes of oxalic acid, malonic acid and methylmalonic acid also exhibit the absorption bands based on the amino group and the carbonyl group.

In addition, the electronic spectrum of the products obtained in the above-described Examples (see Table 5 below) is also explained hereinafter.

Cis-dichloro(cis-1,2-diaminocyclohexane)platinum (II) is characterized by the electronic spectrum having an absorption maximum at 33 KK and a shoulder at 28 KK and 37 KK.

Cis-dichloro(trans-l-1,2-diaminocyclohexane)platinum (II) gives a rise to the almost same electronic spectrum as in cis-dichloro(trans-d-1,2-diaminocyclohexane)platinum (II). Therefore, it is impossible to make these complexes distinct from each other.

The electronic spectrum of cis-oxalato(cis-1,2-diaminocyclohexane)platinum (II) exhibits a shoulder at 31 KK, 39 KK and 49 KK but no absorption maximum. Cis-malonato(cis-1,2-diaminocyclohexane)platinum (II) gives a rise to the almost same spectrum as in cis-methylmalonato(cis-1,2-diaminocyclohexane)platinum (II). That is, cis-malonato(cis-1,2-diaminocyclohexane)platinum (II) exhibits a shoulder at 31 KK and 43 KK but no absorption maximum.

Table 4

(Platinum (II) Complexes of 1,2-Diaminocyclohexane Isomers)

Formula $$\text{cis-}\left[\begin{array}{c}A\\ \diagdown\\ A\end{array}\text{Pt(II)}\begin{array}{c}X\\ \diagup\\ X\end{array}\right]$$

| Compound No. | $\begin{bmatrix}A\diagdown\\ A\diagup\end{bmatrix}$ | $\begin{array}{c}\diagup X\\ \diagdown X\end{array}$ | Elementary Analysis Value | | | | | |
|---|---|---|---|---|---|---|---|---|
| | | | Found | | | Calculated | | |
| | | | H(%) | C(%) | N(%) | H(%) | C(%) | N(%) |
| 1 | 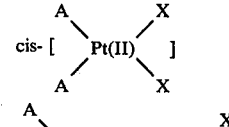 cis- | Cl, Cl | 3.7 | 18.9 | 7.3 | 3.7 | 18.7 | 7.5 |
| 2 | 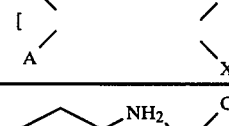 trans-d- | Cl, Cl | 3.7 | 18.9 | 7.3 | 3.8 | 18.7 | 7.1 |
| 3 | 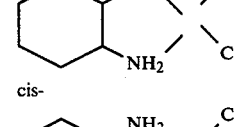 trans-l- | Cl, Cl | 3.7 | 18.9 | 7.3 | 3.7 | 18.7 | 7.5 |

Table 4-continued
(Platinum (II) Complexes of 1,2-Diaminocyclohexane Isomers)

Formula $$cis\text{-}\left[\begin{array}{c}A\\\diagup\\A\end{array}Pt(II)\begin{array}{c}X\\\diagdown\\X\end{array}\right]$$

| Compound No. | A\—A | X\—X | Elementary Analysis Value | | | | | |
|---|---|---|---|---|---|---|---|---|
| | | | Found | | | Calculated | | |
| | | | H(%) | C(%) | N(%) | H(%) | C(%) | N(%) |
| 4 | (1,2-diaminocyclohexane) | oxalato | 3.5 | 24.2 | 7.0 | 4.1 | 23.7 | 7.0 |
| 5 | cis- (1,2-diaminocyclohexane) | oxalato | 3.5 | 24.2 | 7.0 | 3.6 | 24.1 | 7.0 |
| 6 | trans-d- (1,2-diaminocyclohexane) | oxalato | 3.5 | 24.2 | 7.0 | 3.6 | 24.0 | 6.9 |
| 7 | trans-l- (1,2-diaminocyclohexane) | malonato | 4.0 | 26.3 | 6.8 | 3.5 | 26.1 | 7.0 |
| 8 | cis- (1,2-diaminocyclohexane) | malonato | 4.0 | 26.3 | 6.8 | 3.8 | 26.1 | 7.0 |
| 9 | trans-d- (1,2-diaminocyclohexane) | malonato | 4.0 | 26.3 | 6.8 | 3.8 | 26.2 | 7.1 |
| 10 | trans-l- (1,2-diaminocyclohexane) | methylmalonato | 4.3 | 28.2 | 6.6 | 4.4 | 28.2 | 6 |
| 11 | cis- (1,2-diaminocyclohexane) | methylmalonato | 4.3 | 28.2 | 6.6 | 4.1 | 27.8 | 6.6 |
| 12 | trans-d- (1,2-diaminocyclohexane) | methylmalonato | 4.3 | 28.2 | 6.6 | 4.4 | 28.0 | 6.3 |
| 13 | trans-l- (1,2-diaminocyclohexane) | Uracil | | | | | | |

Table 4-continued (Platinum (II) Complexes of 1,2-Diaminocyclohexane Isomers)

Formula $$cis-\left[\begin{array}{c}A\\ \diagdown\\ A\end{array}Pt(II)\begin{array}{c}X\\ \diagup\\ X\end{array}\right]$$

| Compound No. | A⟋ ⟍A | X⟋ ⟍X | Elementary Analysis Value | | | | | |
|---|---|---|---|---|---|---|---|---|
| | | | Found | | | Calculated | | |
| | | | H(%) | C(%) | N(%) | H(%) | C(%) | N(%) |
| 14 | cis- (cyclohexane with NH₂, NH₂) | Uracil | | | | | | |
| 15 | trans-d- (cyclohexane with NH₂, NH₂) | Uracil | | | | | | |
| | trans-l- | | | | | | | |

TABLE 5

(Electronic Spectrum of Platinum (II) Complexes of 1,2-Diaminocyclohexane Isomers)

| Compound No. | band 1 | band 2 | band 3 |
|---|---|---|---|
| 1 | 28KK*(1.40)** | 33.4KK(2.26)** | 37KK*(2.09)** |
| 2 | 28KK*(1.51)** | 33.1KK(2.22)** | 37KK*(2.05)** |
| 3 | 28KK*(1.51)** | 33.1KK(2.22)** | 37KK*(2.05)** |
| 4 | 31KK (2.46) | 39KK (3.34) | 50KK (3.80) |
| 5 | 31KK (2.48) | 39KK (3.36) | 49KK (3.80) |
| 6 | 31KK (2.48) | 39KK (3.36) | 49KK (3.80) |
| 7 | 31KK (1.67) | 43KK (3.50) | |
| 8 | 31KK (1.70) | 43KK (3.52) | |
| 9 | 31KK (1.70) | 43KK (3.52) | |
| 10 | 31KK (1.73) | 43KK (3.60) | |
| 11 | 31KK (1.71) | 43KK (3.60) | |
| 12 | 31KK (1.71) | 43KK (3.60) | |

*shoulder
**logε

Reference Example

To a solution of 0.22 mole of commercially available 1,2-diaminocyclohexane (a product of Tokyo Kasei K.K.) in 160 ml of methanol was added a solution of 26 g (0.11 mole) of $NiCl_2 \cdot 6H_2O$ in 440 ml of methanol, and the resulting solution was then allowed to react at room temperature for 2 hours with stirring. The thus obtained yellow precipitate was filtered, thoroughly washed with methanol and then air-dried to obtain 7.9 g of $Ni(cis-diaminocyclohexane)_2Cl_2$. To the filtrate was added 35 ml of 6 N HCl, and the resulting solution was adjusted to the pH of 4.2 to 4.5 with 15% NaOH. The thus obtained bluish-purple precipitate was filtered, thoroughly washed with water and then air-dried to obtain 18.1 g of $Ni(trans-diaminocyclohexane)_2(H_2O)_2Cl_2$.

The above-described yellow $Ni(cis-diaminocyclohexane)_2 \cdot Cl_2$ was dissolved in 15 ml of 6 N $H_2SO_4$ and concentrated under reduced pressure. 80 ml of ethanol was then added thereto to form a colorless precipitate. The thus obtained precipitate was filtered, thoroughly washed with ethanol and then air-dried to obtain 8.4 g of cis-diaminocyclohexane·$H_2SO_4$. This product was dissolved in a small amount of water. An excess amount of 25% NaOH was added to the resulting mixture to liberate cis-diaminocyclohexane followed by subjecting to the extraction with chloroform. The resulting chloroform solution was dried over $K_2CO_3$ and distilled under reduced pressure to obtain 3.2 g of cis-diaminocyclohexane as a colorless liquid.

Rf=0.58 bp.=39°-41° C./2 mmHg

Additionally, to the above-described purple $Ni(trans-diaminocyclohexane)_2H_2O)_2Cl_2$ was added 30 ml of 6 N HCl and concentrated under reduced pressure. 150 ml of ethanol and 150 ml of acetone were added thereto to form a colorless precipitate. The thus obtained precipitate was filtered, thoroughly washed with ethanol and acetone and then air-dried to obtain 14.6 g of trans-diaminocyclohexane·2HCl. The liberation of this product was carried out in the same manner as was used in the formation of the cis-isomer to obtain 5.3 g of trans-diaminocyclohexane as a colorless liquid.

Rf=0.45 bp.=41°-42° C./2 mmHg

The Rf value was measured by means of a silica gel thin layer chromatography using, as a developer, a mixed solution of ethanol, tetrahydrofuran, diethylamine and water with a mixing ratio of 6:3:1:1 by volume.

Nextly, the resolution from the trans-compound into the d-isomer and l-isomer was carried out in the following manner.

To 5.3 g of trans-1,2-diaminocyclohexane was added 10 ml of water, and the resulting solution was heated to 90° C. to complete the dissolution. 3.3 g of d-oxalic acid and 2.0 ml of glacial acetic acid was then gradually added thereto. After completion of the addition, the resulting mixture was cooled to 0° C. for about 12 hours to obtain {trans-l-1,2-diaminocyclohexane $H_2$} {d-oxalic acid}. This was recrystallized from water to obtain 2.54 g of a product having the following physical values.

| | C % | H % | N % |
|---|---|---|---|
| Calculated: | 45.49 | 7.74 | 10.74 |
| Found: | 45.45 | 7.63 | 10.60 |
| $[\alpha]_D^{20} = +12.2°$ (1% $H_2O$) | | | |

This product was further dissolved in a small amount of water. 1.5 g of KOH was then added thereto to liberate trans-l-1,2-diaminocyclohexane followed by quickly carrying out the extraction with diethyl ether. After evaporating off the diethyl ether, the resultant was distilled under reduced pressure in a nitrogen stream to obtain 2.3 g of trans-l-1,2-diamino-cyclohexane as a colorless liquid having a boiling point of 41°–42° C./2 mmHg.

To the mother liquor from which trans-l-1,2-diaminocyclohexane had been separated was added 4.9 g of d-oxalic acid to obtain 2.3 g of {trans-d-1,2-diaminocyclohexane $H_2$} {d-oxalic acid.H}, in the same manner as was used in the separation of the trans-l-isomer. The thus obtained product was found to have the following physical values.

|  | C % | H % | N % |
|---|---|---|---|
| Calculated: | 38.85 | 6.54 | 6.51 |
| Found: | 38.89 | 6.53 | 6.48 |

$[\alpha]_D^{20} = +25.8°$ (1% $H_2O$)

2.1 g of trans-d-1,2-diaminocyclohexane was also obtained in the same manner as described above. This product was found to have a boiling point of 41° to 42° C./2 mmHg.

While the invention has been described in detail and with reference to specific embodiments thereof, it will be apparent to one skilled in the art that various changes and modifications can be made therein without departing from the spirit and scope thereof.

What is claimed is:
1. Cis-oxalato(trans-l-1,2-diaminocyclohexone)-platinum (II).

* * * * *